(12) United States Patent
Guoin

(10) Patent No.: US 10,626,036 B1
(45) Date of Patent: *Apr. 21, 2020

(54) HYPER-OXYGENATED WATER COMPOSITIONS AND RELATED METHODS AND SYSTEMS

(71) Applicant: PERFECT WATER WORLDWIDE, LLC, Montecito, CA (US)

(72) Inventor: Kenneth J. Guoin, Santa Barbara, CA (US)

(73) Assignee: PERFECT WATER WORLDWIDE, LLC, Montecito, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/727,560

(22) Filed: Oct. 6, 2017

(51) Int. Cl.
| | |
|---|---|
| C02F 9/00 | (2006.01) |
| C02F 1/78 | (2006.01) |
| C02F 1/44 | (2006.01) |
| C02F 1/42 | (2006.01) |
| C02F 1/32 | (2006.01) |
| A61K 9/00 | (2006.01) |
| A61K 33/00 | (2006.01) |
| C01B 5/00 | (2006.01) |
| C02F 103/02 | (2006.01) |

(52) U.S. Cl.
CPC ............. *C02F 9/00* (2013.01); *A61K 9/0014* (2013.01); *A61K 33/00* (2013.01); *C01B 5/00* (2013.01); *C02F 1/32* (2013.01); *C02F 1/42* (2013.01); *C02F 1/441* (2013.01); *C02F 1/78* (2013.01); *C02F 2103/026* (2013.01); *C02F 2201/78* (2013.01)

(58) Field of Classification Search
None
See application file for complete search history.

(56) References Cited

U.S. PATENT DOCUMENTS

| | | | |
|---|---|---|---|
| 2,907,174 A | | 10/1959 | Hendal |
| 4,230,571 A | * | 10/1980 | Dadd ...................... C02F 1/325 210/760 |
| 5,431,810 A | * | 7/1995 | Russo .................... B01D 17/02 210/104 |
| 5,858,430 A | * | 1/1999 | Endico .................. A23L 3/3409 422/21 |
| 6,063,295 A | * | 5/2000 | Williams ................. A01K 7/00 210/109 |
| 6,284,293 B1 | | 9/2001 | Crandall et al. |
| 6,386,751 B1 | | 5/2002 | Wootan et al. |
| 6,521,248 B1 | | 2/2003 | Holloway et al. |
| 7,806,584 B2 | | 10/2010 | Wootan et al. |
| 8,550,696 B2 | | 10/2013 | Ebers et al. |
| 8,771,524 B2 | | 7/2014 | Vorage et al. |
| 2007/0286795 A1 | | 12/2007 | Chiba et al. |
| 2012/0085687 A1 | * | 4/2012 | Simonette ............ B01D 61/025 210/96.2 |
| 2013/0041312 A1 | | 2/2013 | Eckert |
| 2014/0166498 A1 | * | 6/2014 | Orolin ................... C02F 1/4672 205/743 |

FOREIGN PATENT DOCUMENTS

CN 203606310 U * 5/2014

OTHER PUBLICATIONS

Battino, R., T.R. Rettich, and T. Tominaga, "The solubility of oxygen and ozone in liquids". Journal of physical and chemical reference data, 1983. 12(2): pp. 163-178.
Biocera Catalogue, published by Dr. Jeon Hyoung-Tag, Biocera Co. Ltd., South Korea, accessed on May 13, 2017 at www.biocera.co.kr. 30 pages.
Das, C. and P.D. Olmsted, "The physics of stratum corneum lipid membranes", Philosophical Transactions of The Royal Society, Apr. 2016. 374(2072): pp. 1-17.
Dr. Jeffrey McCombs, "The Physiology of Oxygenated Water". May 2017. 4 pages.
"Dr. Otto Heinrich Warburg Nobel Prize Winner *The Root Cause of Cancer*". 1 page.
Ebina, et al. "Oxygen and Air Nanobubble Water Solution Promote the Growth of Plants, Fishes, and Mice" Osaka University, PLOS One, vol. 8, Issue 6, Jun. 2013. 7 pages.
Eucerin, "Understanding skin", accessed on Jun. 5, 2017 at <http://www.eucerin.sg/about-skin/basic-skin-knowledge/skin-structure-and-function.> 15 pages.
"Hyperbaric oxygen therapy", Mayo Clinic, accessed on May 24, 2017 at <http://www.mayoclinic.org/tests-procedures/hyperbaric-oxygen-therapy/basics/definition/prc-20019167>. Nov. 2014: 3 pages.
Ignatov, I. and O. Mosin, "Structural Mathematical Models Describing Water Clusters". Published by The International Institute for Science, Technology and Education, vol. 3, No. 11, 2013. pp. 72-88.
Kaqun Hungary *Oxygenated Water Research Studies*. "Report about effects of Kaqun water on the speed of cognitive functions"; Kocsis, et al. "Study on the effect of Kaqun water on antioxidant capacity"; Biro, et al. "The effect of KAQUN-water on the immune parameters of healthy volunteers", National Institute of Chemical Safety, 2009-12. www.kaqun.sk/en/studies. 5 pages.
Kasai, Y., et al., "The $H_2O$—$O_2$ water vapour complex in the Earth's atmosphere". Atmospheric Chemistry and Physics, Aug. 2011. 11(16): pp. 8607-8612.

(Continued)

*Primary Examiner* — Monica A Shin
(74) *Attorney, Agent, or Firm* — Steinfl + Bruno LLP

(57) ABSTRACT

A hyper-oxygenated water composition comprising water and 10 ppm to 50 ppm of molecular oxygen, methods and systems of making and using the hyper-oxygenated water composition are described. The hyper-oxygenated water composition was made by pre-filtering and filtering by reverse osmosis of a source water, ozonolyzing and vortexing with oxygen with the water, ultraviolet irradiating and treating with hydrogen peroxide the water. The hyper-oxygenated water composition can be used for general improvement of human well-being and prevention and treatment of diseases by oral or transcutaneous administration of the hyper-oxygenated water composition.

12 Claims, 10 Drawing Sheets

(56) References Cited

OTHER PUBLICATIONS

Ladizinsky, D. and D. Roe, "New Insights Into Oxygen Therapy for Wound Healing. Wounds", 2010. 22(12): pp. 294-300.
Lambrechts et al. "Normalizing tumor oxygen supply could be key factor in the fight against cancer", Nature, Aug. 2016. 1 page.
Madagascar Minerals "Rose Quartz Spheres" website, accessed Oct. 16, 2017. Tucson, AZ. 2003-2017.<www.madagascarminerals.com/cat_rose_quartz_spheres1.cfm>.
Potts, R.O. and M.L. Francoeur, "Lipid biophysics of water loss through the skin." Proceedings of the National Academy of Sciences, May 1990. 87(10): p. 3871-3873.
Shimadzu, Application News, Nano Particle Size Analyzer: SALD-7101, No. 4, Downloaded from <http://www.ssi.shimadzu.com/products/literature/testing/microbubbles%20nanobubbles%20red.pdf> accessed on Jul. 24, 2017. pp. 1-3.
Spivey, N., "Application Note, Atomic Absorption, Analysis of Major Elements in Drinking Water Using FAST Flame Sample Automation for Increased Sample Throughput". 2015: pp. 1-5.
Stillinger, F.H., "Theory and molecular models for water". Adv. Chem. Phys, 1975. 31(1). 101 pages.
Stücker, M., et al., "The cutaneous uptake of atmospheric oxygen contributes significantly to the oxygen supply of human dermis and epidermis." The Journal of physiology, 2002. 538(3): pp. 985-994.
"Thermo Scientific Orion Chlorine XP Water Quality Analyzer" UM-269688-001 Revision C. Nov. 2016: pp. 1-57.
Uchida, T., et al., "Effect of NaCl on the Lifetime of Micro-and Nanobubbles". Nanomaterials, Feb. 2016. 6(2): 10 pages.
United States Environmental Protection Agency, Method 8265, Volatile Organic Compounds in Water, Soil, Soil Gas, and Air by Direct Sampling Ion Trap Mass Spectrometry (DSITMS). Mar. 2002: pp. 1-64.
van Smeden, J. and J.A. Bouwstra, "Stratum corneum lipids: their role for the skin barrier function in healthy subjects and atopic dermatitis patients", in Skin Barrier Function. Feb. 2016, Karger Publishers. 2 pages (abstract only).
Wikipedia, "Air pollution", accessed on May 26, 2017 at <https://en.wikipedia.org/wiki/Air_pollution>. 2017: pp. 1-26.
Wikipedia, Metastability, accessed on Jun. 5, 2017 at <https://en.wikipedia.org/wiki/Metastability>. 2017. pp. 1-5.
Yeomans, et al. "Oxygen absorption by skin exposed to oxygen supersaturated water." Can J Physiol. Pharmacol. May 2012. 1 page (abstract only).
Yeomans, et al. "Skin oxygen tension is improved by immersion in oxygen-enriched water." Int. J. Cosmet. Sci. Dec. 2013. 1 page (abstract only).
Yin, H., et al., "Metastable water clusters in the nonpolar cavities of the thermostable protein tetrabrachion". Journal of the American Chemical Society, 2007. 129(23): pp. 7369-7377.
Barret, S., FTC Attacks 'Stabilized Oxygen Claims,' accessed at<https://www.quackwatch.org/04ConsumerEducation/News/vitamino.html>May 2000. 3 pages.
Bickers, D.R., et al., "Oxidative Stress in the Pathogenesis of Skin Disease," Journal of Investigative Dermatology vol. 126(12):2465-75.Jan. 2006. 11 Pages.
Bunkin., N.F., et al., "Structure of the Nanobubble Clusters of Dissolved air in Liquid Media," J Biol Phys. vol. 38(1):121-52. Jan. 2012. 32 Pages.
Cameron., R., "Tiny Bubbles" *ACCJ Journal*, pp. 35-37.Jun. 2005. 3 Pages.
Chaplin., M., "Water Structure and Science: Nanobubbles (ultrafine bubbles)," accessed at< http://www1.lsbu.ac.uk/water/nanobubble.html>.Jan. 2007. 13 Pages.
Chougule , S.S., et al., "Comparative Study on Heat Transfer Enhancement of Low Volume Concentration of AL2O3—Water and Carbon Water Nanotube—Water Nanofluids in Laminar Regime Using Helical Screw Tape Inserts," *Exp. Heat Transfer*, vol. 28(1)pp. 17-36.Aug. 2015.21 Pages.

Connor, M.J., et al., "Depletion of Cutaneous Glutathione by Ultraviolet Radiation," *Photochemistry and Photobiology*, vol. 46(2). pp. 239-245.Aug. 1987. 7 Pages.
Duntas, L.H., et al., "Selenium and Inflammation—Potential Use and Future Perspectives" US Endocrinology, 11: 97-102.Jan. 2015.6 Pages.
Harch, P.G., "Hyperbaric oxygen in chronic traumatic brain injury: oxygen, pressure, and gene therapy." Medical Gas Research vol. 5(9). Jul. 14, 2015. 4 pages.
Idec, "What are Ultrafine Bubble," Website accessed at< https://www.idec.com/home/finebubble/bubble01.html>Jan. 2017. 3 pages.
Kim, A.L. et al., "Role of p38 MAPK in UVB-Induced Inflammatory Responses in the Skin of SKH-1 Hairless Mice," Journal of Investigative Dermatology vol. 124(6):1318-25.Jun. 2005. 8 Pages.
Lee, Y.S., et al., "Long Course Hyperbaric Oxygen Stimulates Neurogenesis and Attenuates Inflammation after Ischemic Stroke," Mediators of Inflammation vol. 2013, Article ID 512978, 13 pages. Jan. 2013. 14 Pages.
Li, H., et al., "Antagonistic Effects of P53 and HIF1A on MicroRNA-34-a Regulation of PPP1R11 and STAT3 and Hypoxia-induced Epithelial to Mesenchymal Transition in Colorectal Cancer Cells," American Gastroenterological Association vol. 153(2): 505-20. Aug. 2017. 17 pages.
Lower, S., "H2O: A Gentle Introduction to Water and its Structure," accessed at< http://www.chem1.com/acad/sci/aboutwater.html> on Sep. 5, 2019. 15 Pages.
Ludwig-Maximilians-Universität München. "Cancer Metastasis: The unexpected perils of hypoxia." ScienceDaily, May 11, 2017, Accessed at https://www.sciencedaily.com/releases/2017/05/170511113523.htm>. 5 Pages.
Mayo Clinic. "Skin cancer on the rise." ScienceDaily, May 15, 2017. Accessed at http://www.sciencedaily.com/releases/2017/05/170515141000.htm>. 5 Pages.
McColl, A., et al., "TLR7-mediated skin inflammation remotely triggers chemokine expression and leukocyte accumulation in the brain," Journal of Neuroinflammation vol. 13 (102).May 2016. 16 Pages.
"Naneau: Breathing Life into Water," 2019 Website. Accessed at <http://www.inspiredwaters.com/ on Sep. 2019. 11 Pages.
"Naneau O2 Water," Jan. 2019 Marketing materials by Naneau. 26 Pages.
Naneau Oxygen Nanobubbles Website: Home page, About Naneau, and the Science behind Naneau. Accessed fromhttps://naneauhealth.com/> on Nov. 21, 2019. 26 Pages.
Pansky, B., "Review of Medical Embryology Book, Chapter 25: Germ Layers and their Derivatives," accessed at< https://discovery.lifemapsc.com/library/review-of-medical-embryology/chapter-25-germ-layers-and-their-derivativesonSep. 5, 2019. 2 Pages.
Reelfs, O., et al., "Ultraviolet A Radiation-Induced Immediate Iron Release is a Key Modulator of the Activation of NF-κB in Human Skin Fibroblasts," Journal of Investigative Dermatology vol. 122(6):1440-47. Jun. 2004. 8 Pages.
Restriction Requirement for U.S. Appl. No. 15/727,470, filed Oct. 6, 2017 on behalf of Perfect Water Worldwide, LLC, dated Oct. 28, 2019. 6 pages.
Scheuplein, R.J., "Mechanism of Percutaneous Absorption: II. Transient Diffusion and the Relative Importance of Various Routes of Skin Penetration," Journal of Investigative Dermatology vol. 48(1): 79-88.Jan. 1967. 10 pages.
"State of the Air 2016," Report by the American Lung Association, accessed at< http://www.lung.org/assets/documents/healthy-air/state-of-the-air/sota-2016-full.pdfinJan. 2016. 157 Pages.
Xi., C., et al., "Reduction of Ammonia Emission in Chicken Farms by Improved Water Systems," Jan. 2011. Accessed from <http://www.inspiredwaters.com/naneau-science-studies/ on Sep. 2019. 2 Pages.
Yurchenko., S.O., et al., "Ion-Specific and Thermal Effects in the Stabilization of the Gas Nanobubble Phase in Bulk Aqueous Electrolyte Solutions," Langmuir 32 (43):11245-11255.Jun. 2016. 12 Pages.
Zhang, Q., et al., "Hyperbaric Oxygen Attenuates Apoptosis and Decreases Inflammation in an Ischemic Wound Model," J Invest Dermatol, 128(8):2102-12.Mar. 2008. 11 Pages.

(56) References Cited

OTHER PUBLICATIONS

Zhao, B., et al., "Hyperbaric oxygen attenuates neuropathic pain and reverses inflammatory signaling likely via the Kindlin-1/Wnt-10a signaling pathway in the chronic pain injury model in rats," J Headache Pain, 18(1).Jan. 5, 2017. 8 Pages.

* cited by examiner

PRIOR ART

PRIOR ART

PRIOR ART o number of $O_2$ stabilized by a cluster of w number $H_2O$

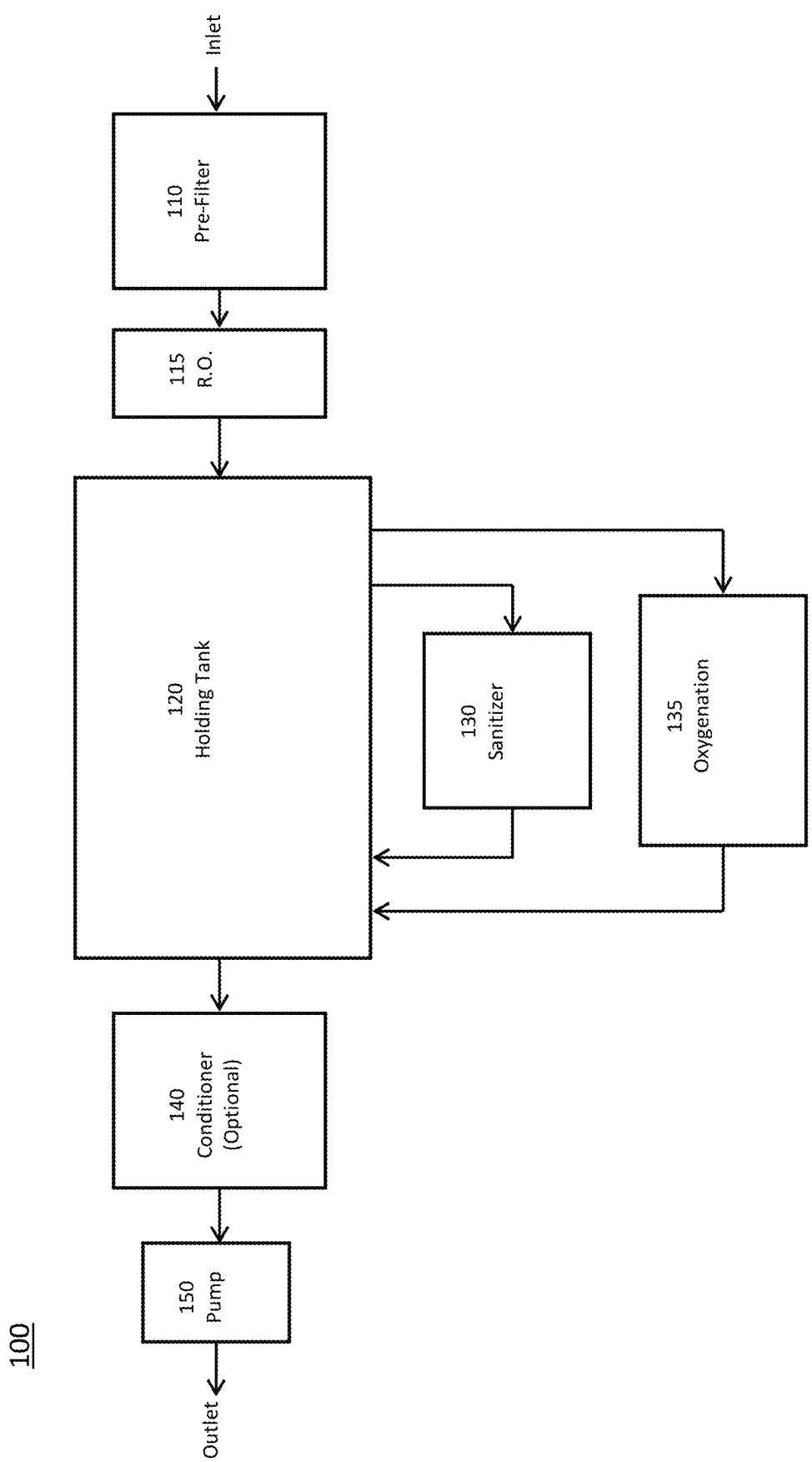

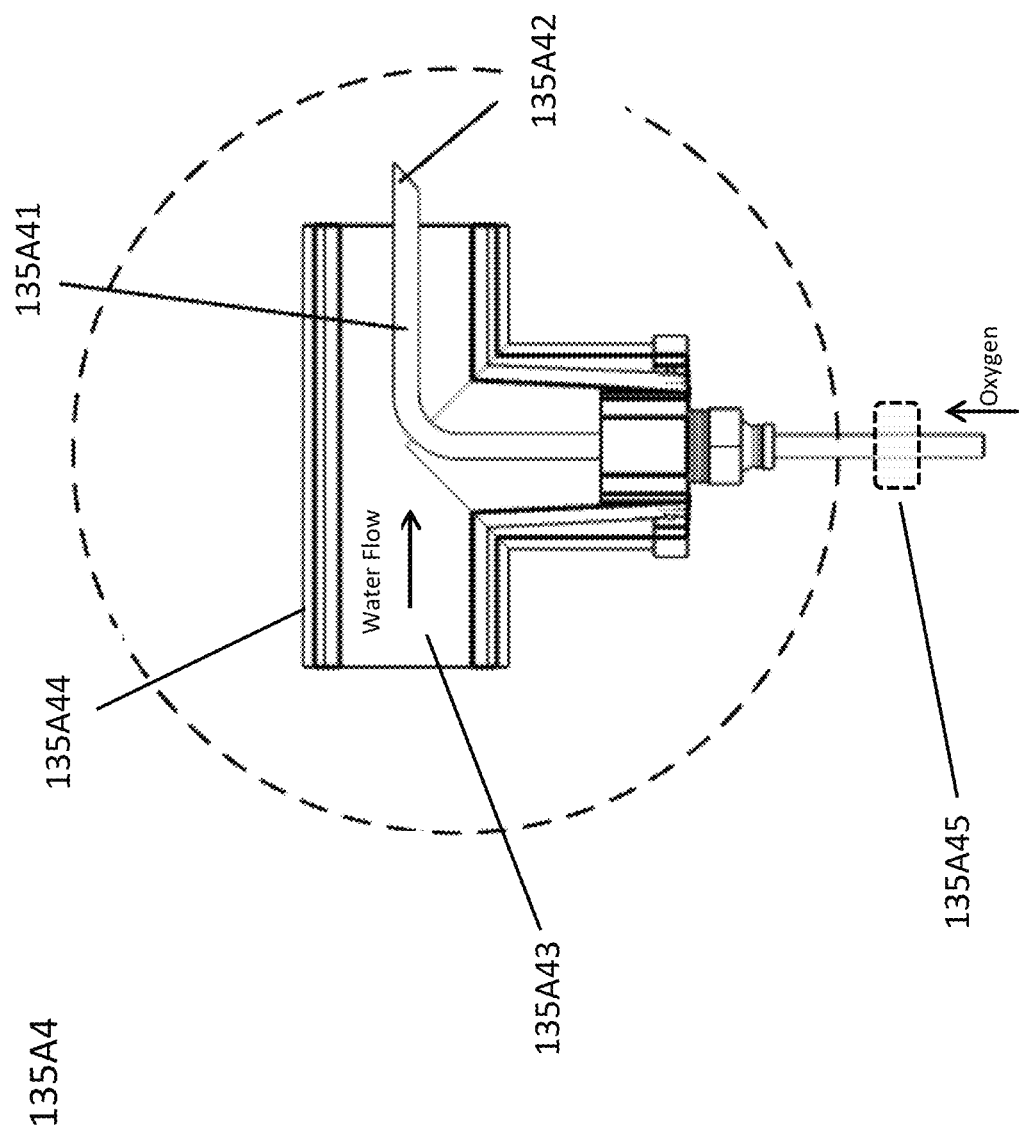

HYPER-OXYGENATED WATER COMPOSITIONS AND RELATED METHODS AND SYSTEMS

CROSS REFERENCE TO RELATED APPLICATIONS

The present application is related to U.S. application Ser. No. 15/727,217 entitled "SELF-CONTAINED WATER SYSTEM" filed on even date herewith, U.S. provisional Application No. 62/569,432 entitled "VORTEXING CHAMBER AND SYSTEM" filed on even date herewith, and U.S. application Ser. No. 15/727,470 entitled "HYPER-OXYGENATED SOAKING SPA SYSTEM" filed on even date herewith, each of which is incorporated herein by reference in its entirety.

TECHNICAL FIELD

The present disclosure relates generally to oxygenated water compositions and related methods and systems. In particular, the present disclosure provides a process of making hyper-oxygenated water compositions and related systems and methods of use thereof.

BACKGROUND

Our body's two greatest needs are for oxygen and water. Life depends on oxygen and water. With the Industrial Revolution, much of world's fresh water became polluted and denatured. On the other hand, air pollution has increasingly gripped the attention of our generation.

Indoor air pollution and poor urban air quality are listed as two of the world's worst toxic pollution problems in the 2008 Blacksmith Institute World's Worst Polluted Places report. According to the 2014 WHO report, air pollution in 2012 caused the deaths of around 7 million people worldwide, an estimate roughly matched by the International Energy Agency. [1].

Throughout history, it has been recognized that wounds heal faster if a patient is transported from thin mountain air to a richer atmosphere (e.g., a low-lying valley). In modern times, oxygen has been recognized as the element most essential to healing. Clinicians are now able to diagnose oxygen deficiency and administer oxygen therapy with increasingly advanced mechanisms and devices. [2].

Hyperbaric oxygen therapy involves breathing pure oxygen (i.e., 100% oxygen) in a pressurized room or tubular chamber. Conditions treated with hyperbaric oxygen therapy include serious infections, bubbles of air in your blood vessels, and wounds that would not heal as a result of diabetes or radiation injury. [3].

It was described that oxygen level in water can be increased to approximately 50 to 60 ppm when it flows in a spiraling manner in an oxygen-rich environment. [4]. Oxygen and air nanobubble water solution was also reported to be bioactive effects upon animals and plants. [5], [6].

There has been interest in using aqueous oxygenation to treat disease condition and improve human wellness. [7], [8].

However, there remains an unmet need for a hyper-oxygenated water composition for maintenance and enhancement of animal well-being and prevention and treatment of diseases for delivery of oxygen in water to an animal such as a human.

SUMMARY

Described herein are hyper-oxygenated water compositions and related methods, and systems that in some embodiments permit delivery of oxygen in water to an animal.

According to a first aspect, a hyper-oxygenated water composition is described. The hyper-oxygenated water composition comprises liquid water, wherein the liquid water is produced by a process of oxygenation to contain a total molecular oxygen in an amount of 10 to 50 ppm and a total dissolved solid of 4 to 200 ppm, at a temperature ranging from 4° C. to 40° C. In some embodiments, the hyper-oxygenated water composition contains total chlorine in an amount equal to or less than 1 ppm. In some embodiments, the hyper-oxygenated water composition contains volatile organic compounds (VOCs) in an amount equal or less 1 ppm. In some embodiments, the hyper-oxygenated water composition has the total dissolved solid containing calcium of 1 ppm to 50 ppm, phosphate of 1 ppm to 50 ppm, zinc of 1 ppm to 20 ppm. [9].

In a second aspect, a process of making a hyper-oxygenated water composition is described, the process comprising: providing a source for water having a total dissolved solid of up to 1000 ppm where in the water is subject to steps: (a) pre-filtering the water; (b) purifying the water by absorption; (c) at least partially removing ion from the water by ion exchange; (d) filtering the water by reverse osmosis, wherein the water is caused to flow to a holding tank, for example, a hot tub; (e) ozonolyzing the water in step (d) in an independently circulating fluidic circuit comprising the holding tank and an ozone source; (f) radiating the water in step (d) with ultraviolet light in an independently circulating fluidic circuit comprising the holding tank and an ultraviolet light source; (g) adding a hydrogen peroxide aqueous solution to the ultraviolet light radiated water in step (f); (h) mixing the water in step (d) with oxygen gas in a vortexing chamber in an independently circulating fluidic circuit comprising the holding tank and the vortexing chamber. The vortexing chamber comprises: a chamber housing having a main hollow channel, a first end and a second end, and a structural mixing medium having one or more three dimensional solid objects, the solid objects having substantially spherical, cubic, rectangular, cylindrical, polyhedron, tetrahedron, or irregular shape, wherein the structural mixing medium is housed within the chamber housing, configured to mix the water and oxygen when the water and oxygen are passed through the vortexing chamber, resulting in a hyper-oxygenation of the water. The hyper-oxygenated water composition in the holding tank contains a total molecular oxygen in an amount of 10 to 50 ppm and a total dissolved solid of 5 to 200 ppm.

In a third aspect, a method for treating or preventing a condition in a subject, the method comprising: administering to the subject in need of the treating or preventing an effective amount of hyper-oxygenated water composition optionally in combination with at least one pharmaceutical agent in an effective amount thereof, wherein hyper-oxygenated water composition is produced by a process of oxygenation to contain a total molecular oxygen in an amount of 10 to 50 ppm and a total dissolved solid of 4 to 200 ppm.

In some embodiments, administering to the subject is performed transcutaneously.

In a fourth aspect, a system for hyper-oxygenated water composition, the system comprising: a water inlet; a water outlet; a holding tank; a water pre-treatment stage configured to receive water from the water inlet and provide pre-treated water to the holding tank; optionally a water post-treatment stage configured to receive water from the holding tank and provide post-treated water to the water outlet; a water sanitation treatment stage configured to receive water from the holding tank and provide sanitized water to the holding tank; and an oxygenation treatment stage configured to receive water from the holding tank and provide hyper-oxygenated water composition to the holding tank.

As described herein, the system includes the water pre-treatment stage comprising: (a) a pre-filter for the water; (b) an absorbent for the water; (c) an ion exchanger; and (d) a reverse osmosis filter. In some embodiments, the system includes the water sanitation treatment stage comprising: (e) an ozone source for producing ozone configured to be mixed with the water in step (d) in an independently circulating fluidic circuit comprising the holding tank and the ozone source; (f) an ultraviolet light source for producing ultraviolet light configured to radiate the water in step (d) in an independently circulating fluidic circuit comprising the holding tank and the ultraviolet light source; and (g) a source of 35% food grade hydrogen peroxide aqueous solution wherein the hydrogen peroxide aqueous solution is metered to be mixed with the ultraviolet light radiated water in step (f).

The system includes an oxygenation treatment stage comprising: an oxygen gas source, a vortexing chamber in an independently circulating fluidic circuit comprising the holding tank and the vortexing chamber, wherein the vortexing chamber may be configured as: a chamber housing having a main hollow channel, a first end and a second end, and a structural mixing medium having one or more three dimensional solid objects, the solid objects having substantially spherical, cubic, rectangular, cylindrical, polyhedron, tetrahedron, or irregular shape, wherein the structural mixing medium is housed within the chamber housing, configured to mix the water and oxygen when the water and oxygen are passed through the vortexing chamber, resulting in a hyper-oxygenation of the water.

The details of one or more embodiments of the disclosure are set forth in the accompanying drawings and the description below. Other features and objects will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 7 shows a block diagram of a water restructuring system, including a water inlet attached to a water pre-filter, reverse osmosis (R.O.) device fluidically connected to a water reservoir (i.e. a holding tank), a sanitizer forming a first fluidic communication loop with the tank, an oxygenation apparatus forming a second fluidic communication loop with the tank, and optionally a water conditioner fluidically connected to a water reservoir and is connected to a water outlet via a delivery pump.

FIG. 8B illustrates details of an oxygen injector device, according to an embodiment of the present disclosure, configured to inject oxygen into the oxygenation loop.

DETAILED DESCRIPTION

Figure 1:
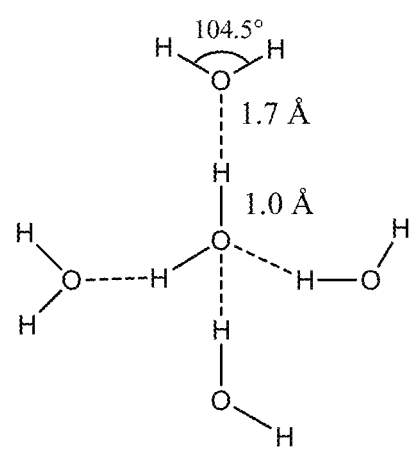
FIG. 1 shows a schematic illustration of water molecule in liquid state. [10], [11].

Described herein are hyper-oxygenated water compositions and related methods, and systems that delivers oxygen in the hyper-oxygenated water compositions to an animal in need thereof.

The term "hyper-oxygenated water" as used herein refers to a water which contains molecular oxygen $O_2$ in a total amount of at least 10 ppm up at a temperature ranging from 4° C. to 50° C.

The molecular oxygen in the hyper-oxygenated water may be present in three different forms, including dissolved oxygen, water clustered oxygen and nanobubble oxygen in water.

As used herein, a "nanobubble" refers to a substantially spherical body of gas having a diameter of 100 nm or less comprising at least two oxygen molecules wherein the substantially spherical body in suspended in liquid water.

As used herein, "dissolved oxygen" refers to oxygen that is homogeneously mixed with water in a thermodynamically stable state and form a single phase of matter.

In contrast to dissolved oxygen and as used herein, "entrapped oxygen" refers to oxygen molecule present in the hyper-oxygenated water composition that is not dissolved in water in a thermodynamic sense but is transiently or kinetically stable for a period of at least 1 day, 1 week, one month, six months, or two years. Without being bound by any theory, the nanoscale, i.e., equal to or less than 100 nm size of oxygen within water cluster and/or nanobubble in water impart stability to the hyper-oxygenated water composition.

In particular, the hyper-oxygenated water compositions as described herein are stable with the loss of entrapped oxygen content being by less than 10%, preferably, less than 5% or less than 1% over a period of at least 1 month, 3 months, 6 months or 1 year.

As used herein, a "water clustered oxygen" refers to an entrapped oxygen molecule that is contained in a cluster of water.

The term "total dissolved solids" (i.e., TDS) is the combined content in parts per million (ppm) by weight of all inorganic and organic substances contained in a liquid in molecular, ionized or micro-granular (colloidal sol) suspended form. The term total dissolved solids as described herein can be measured by gravimetric analysis. Gravimetric methods involve evaporating the liquid solvent and measuring the mass of residues left. This method is particularly suitable when inorganic salts comprise the great majority of TDS.

The term "substantially free" herein refers to presence of a component including ion, molecule or a suspended particulate in a water composition in an amount of less than 1 ppm.

The term "volatile organic compounds" (VOCs) as used herein refers to any organic compound having an initial boiling point less than or equal to 250° C. (482° F.) measured at a standard atmospheric pressure of 101.3 kPa. The amount of volatile organic compounds in water can be measured, for example, by following the method provided by the United States Environmental Protection Agency using mass spectrometry. [13].

The term "animal" as used here in refers to a warm-blooded vertebrate including but not limited to human, horse, cow, goat, sheep, dog, cat, pig, mule, chicken, rabbit, mouse, and rat. A subject as used herein can be a human or another animal.

The term "treatment" as used herein indicates any activity that is part of a medical care for, or deals with, a condition, medically. The terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a symptom or adverse physiological event in a susceptible individual, as well as modulation and/or amelioration of the status of a clinically symptomatic individual by inhibiting or causing regression of a disorder or disease.

The term "prevention" as used herein with reference to a condition indicates any activity which reduces the burden of mortality or morbidity from the condition in an individual.

The term "oral administration" refers to a route of delivering a substance through mouth. For example, water can be orally administered by drinking.

The term "transcutaneous administration" refers to a route of taking a substance through diffusion through skin in a transdermal route. For example, a hyper-oxygenated water can be transcutaneously administered by soaking.

The term "soaking" as used herein refers to immersing at least a part of a subject in a water in a soaking vessel having an open surface and a depth for an interval of time.

A "soaking vessel" as used herein is a container that is capable of holding liquid water and configured for at least partial immersion of any part of the body of an animal in the liquid water. An exemplary soaking vessel a conventional or commercial soaking spa.

For, example, a male human of 20 years age having a body weight of 180 lbs. can be soaking whole body up to the neck in a tub of hyper-oxygenated water with 30 ppm oxygen molecule at 38° C. for 15 min twice a day, once in the morning and once in the evening for a duration of at least one week, one month, six months or life-long.

Liquid water is a dynamic associative-dissociative system, consisting of three to hundreds individual $H_2O$ molecules binding by multiple intermolecular hydrogen bonds, being in a state of dynamic equilibrium. In the dynamic associative-dissociative system, a hydrogen bond is broken and a new hydrogen bond is formed Not only is water capable of forming clusters. Water clusters can also fill in and interact with nonpolar cavities of a protein. [14]. Water permeability through skin is dependent upon the hydrocarbon-chain disorder of stratum corneum (SC) lipids. [15].

In a similar manner as the water-oxygen molecule interaction in the gas phase, it is disclosed herein that water-oxygen interaction exists in liquid water. [12]. Indeed, water is an effective vehicle for transporting dissolved $O_2$ across the skin surface. [16] [17].

FIG. 1 shows a water molecule that is surrounded by four other water molecules through hydrogen bonds between H from one water molecule to O from other water molecules in a liquid state. As illustrated by FIG. 1, the oxygen to hydrogen bond may have a bond length of 1.0 Angstrom and a hydrogen bond may have a distance of 1.7 Angstrom. The dihedral angle between the two covalent O—H bonds of a water molecule may have a value of 104.5°.

Figure 2:
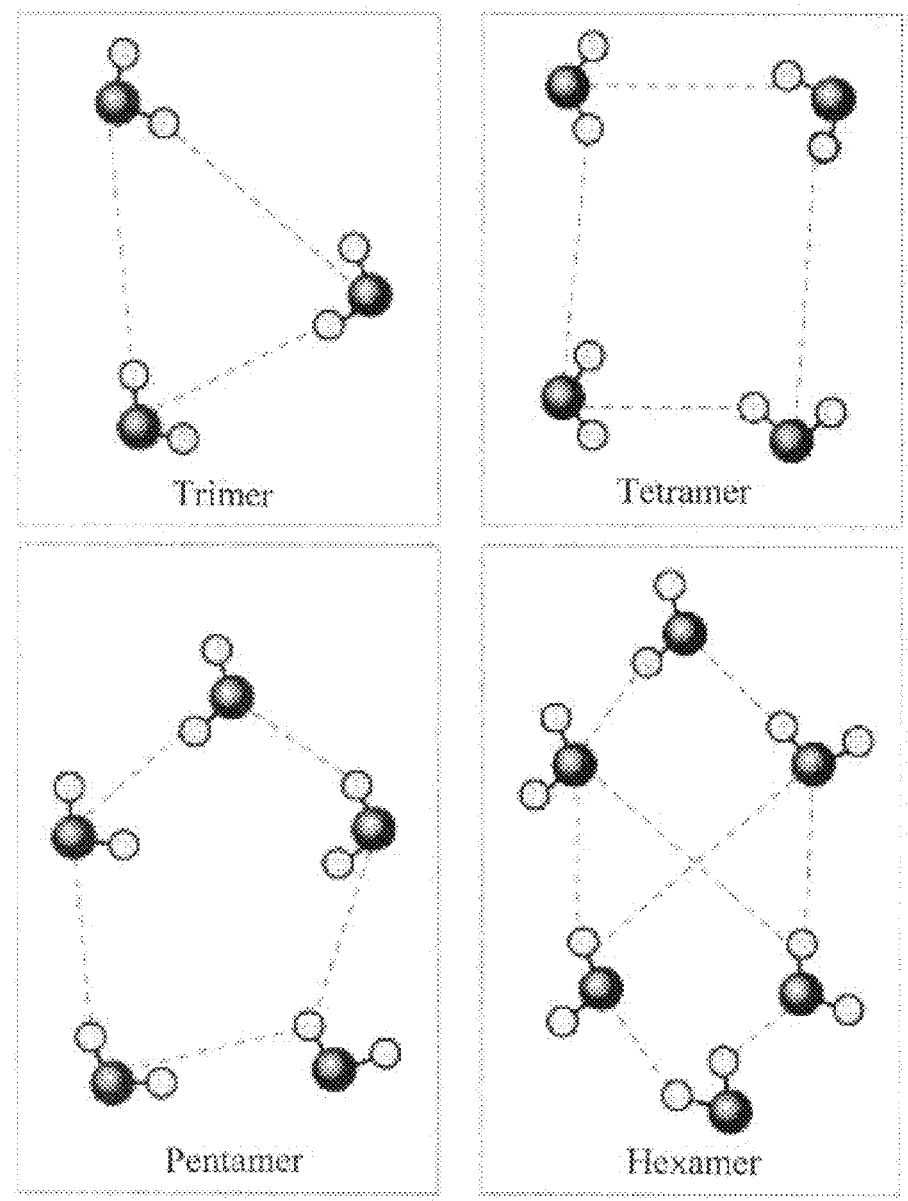
FIG. 2 shows a schematic illustration of water molecule in liquid state. [10].

FIG. 2 shows a schematic illustration of water clusters as a trimer, tetramer, pentamer and hexamer of water. [10].

Figure 3:
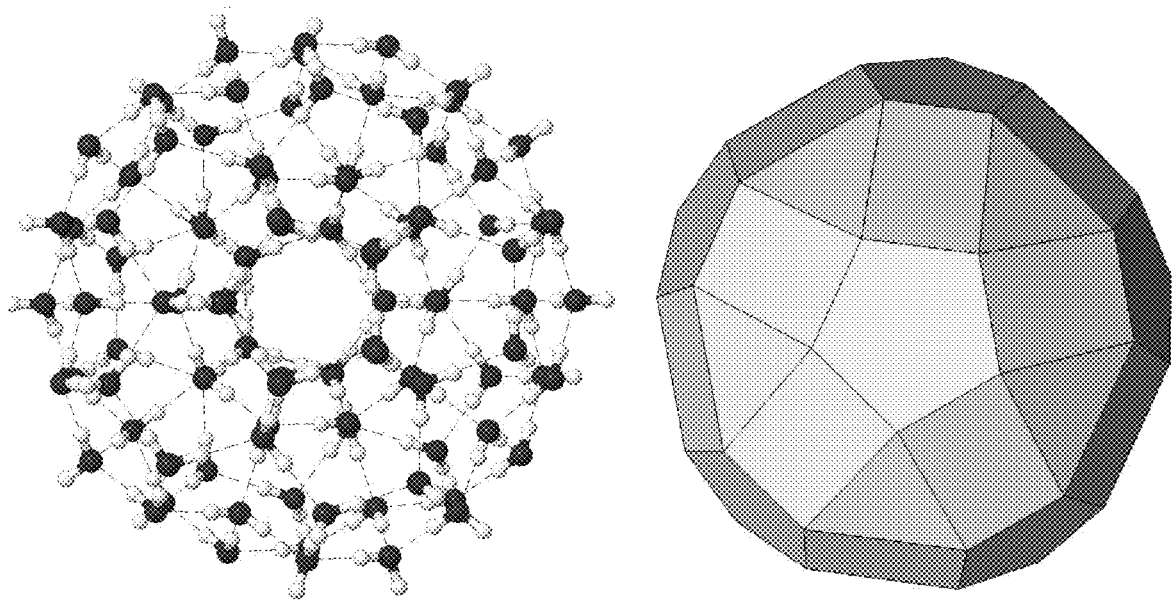
FIG. 3 shows an icosahedral water cluster based on $H_2O$ molecules and the underlying structure. [10].

FIG. 3 shows a icosahedral water cluster based on 100 $H_2O$ molecules and the underlying structure. [10]. It is to be understood that water clusters based on other different numbers of water molecules are feasible including but not limited to 8 to 20, 57, 196, 224, 252, 912, and up to 1820 $H_2O$ molecules. [10].

Figure 4:
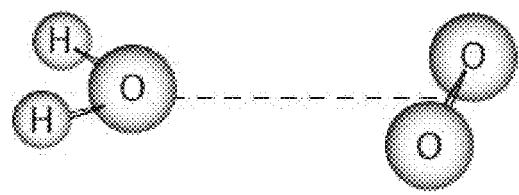
FIG. 4 shows a molecular structure of a van-der Waals complex $H_2O$—$O_2$ in vapor. [12].

FIG. 4 shows a molecular structure of a van-der Waals complex $H_2O$—$O_2$ in vapor. [12]. It is to be understood that similar force present in the vapor between water and oxygen may be present also in liquid water.

Figure 5:
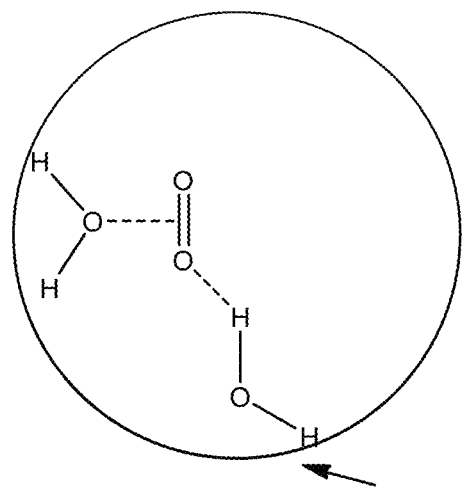
FIG. 5 shows a schematic representation of a van-der Waals complex $O_2(o)$-$H_2O$ (w) cluster in hyper-oxygenated water.

FIG. 5 shows a schematic representation of a van-der Waals complex $O_2(o)$-$H_2O$ (w) cluster in hyper-oxygenated water in one embodiment, in which oxygen molecules was stabilized by a cluster of w water molecules through van-der Waals interaction between oxygen and water, in which o is an integer ranging from 1 to 100 and w is an integer ranging from 5 to 1000. Referring to FIG. 4, the van-der Waals complex $H_2O$—$O_2$ in vapor is also present in the liquid water and oxygen interaction. In addition, due to abundance of water molecules surrounding the oxygen molecule, interaction with additional water molecules are also present which, without being bound by theory, contributes to the overall stabilization of the hyper-oxygenated water composition.

Figure 6:
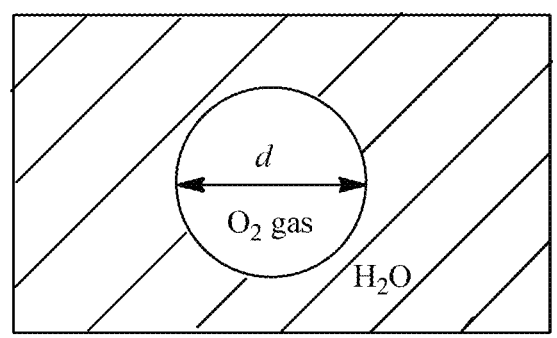
FIG. 6 shows a schematic representation of a $O_2$ nanobubble of a diameter d in $H_2O$ in a hyper-oxygenated water composition.

FIG. 6 shows a schematic representation of a $O_2$ nanobubble of a diameter d in $H_2O$ in a hyper-oxygenated water composition, in which d ranges from 1 nanometer to 10 microns, 10 nanometers to 1 micron, or from 0.1 to 0.1 micron.

It is to be understood that an oxygen nanobubble may coexist in various proportions with a water clustered oxygen, i.e., oxygen water cluster and dissolved oxygen.

FIG. 7 illustrates a functional block diagram of one embodiment of the hyper-oxygenated water system (100) according to the present disclosure which is configured to purify incoming water through an inlet, and optionally restructure, namely, recondition the purified water to deliver, at an outlet, purified, alkaline, ionized, mineral-rich water at a controlled temperature to an entire residential or commercial site.

With continued reference to the hyper-oxygenated water system (100) of FIG. 7, incoming water fed through the inlet is routed to a pre-filtering stage (110) which is configured to soften and pre-filter the incoming water and remove any particles that may damage elements of the next block, the reverse osmosis R.O. stage (115). The pre-filtered and softened water is fed to the reverse osmosis R.O. stage (115) to further reduce total dissolved solids (TDS) in the water to about 4 parts per million (ppm) or less before feeding the water to the holding tank (120).

The low TDS water in the holding tank (120) may in turn be processed according to functionalities provided by at least two separate water treatment loops; the sanitizer loop (130) and the oxygenation loop (135). The sanitizer loop (130) may sanitize the water by disinfecting the water and removing contaminants and other impurities that are not be removed by the preceding blocks. These can include any living contaminants including microorganism such as bacteria, *Salmonella enterica, Campylobacter*, viruses, norovirus, protozoans. The sanitizer loop (130) may further be configured to chill or heat the water and maintain the water temperature at a substantially constant temperature below room temperature (e.g., 8-15 degrees Celsius) or above room temperature (e.g., 35-40 degrees Celsius). As used herein, a room temperature is defined as a temperature at 20 degrees Celsius. Accordingly, the water in the water reservoir (i.e., the holding tank (120)) is a filtered, temperature adjusted by heating or chilling and contaminant free water, therefore substantially devoid of organic and inorganic contaminants.

In some embodiments, the water reservoir (i.e., the holding tank (120)) contains water at a temperature between 30 to 40° C. and is configured for soaking of a subject.

Independent from the sanitizer loop (130), the oxygenation loop (135) may be used to enrich oxygen content of the water in the holding tank (120) by mixing appropriate amount of oxygen with water through a high speed hydraulic system that generates nanobubbles of oxygen and/or clusters of oxygen and water that remain entrapped in the water. Total oxygen concentration, including entrapped and dissolved oxygen of the water in the holding tank (120) may be monitored by an oxygen probe and accordingly kept to a desired concentration by controlling ON/OFF cycles of the oxygenation loop (135) in a closed loop fashion via the feedback from the oxygen probe. Alternatively, an ON/OFF duty cycle of the oxygenation loop (135) may be pre-programmed based on known/expected total entrapped and dissolved oxygen concentration in the holding tank (120).

With further reference to FIG. 7, the holding tank (120) of the hyper-oxygenated water system (100) according to the present teachings is therefore configured to contain constant temperature water that is substantially free of any organic and inorganic contaminants.

The organic contaminants herein include but are not limited to any organic molecule that contains any one of aliphatic, cycloaliphatic, aromatic, polyaromatic, heteroaliphatic, cycloheteroaliphatic, or heteroaromatic group.

The inorganic contaminants include but are not limited to iron, lead, heavy metals, radioactive atoms, chlorine in different oxidation states such as chlorine molecule, chloride, hypochlorite, chlorate, perchlorate, or organochlorine. In some embodiments, the total chlorine in different oxidation states is less than 1 ppm, preferably less than 0.01 ppm.

Furthermore, total entrapped and dissolved concentration of oxygen in the water can be controlled by the oxygenation loop (135) to levels in a range of about 10 mg/L to about 50 mg/L at a temperature up to 40° C.

Delivery of water from the holding tank (120) to the outlet can be triggered via pressure demand or a pressure sensor at the outlet, which causes the delivery pump (150) to activate and send water from the holding tank (120) though the conditioner stage (140) to the outlet for end use. The conditioner stage (140) may condition the water to provide a water composition with a predetermined amount of minerals at a predetermined level of alkalinity (pH value 7.5-9.5), preferably a pH of 8.0.

It was found that a water composition having presence of a predetermined amount of minerals at a predetermined level of alkalinity (pH value 7.5-9.5), preferably a pH of 8.0, was unexpectedly effective and beneficial for treatment of human diseases and maintenance of human well-being as illustrated by examples 8 and 9 of the present disclosure.

It follows that the functional blocks of the hyper-oxygenated water system (100) according to the disclosure herein depicted in FIG. 7 process the incoming water to provide in the holding tank (120) a hyper-oxygenated water composition that is substantially free of any organic and inorganic contaminants or any microorganism at a predetermined temperature, with control of total oxygen amount in the water, which can be optionally re-mineralized and made alkaline for delivery at the outlet. Further implementation details for preparing hyper-oxygenated water composition are described in the following paragraphs.

Figure 8A:
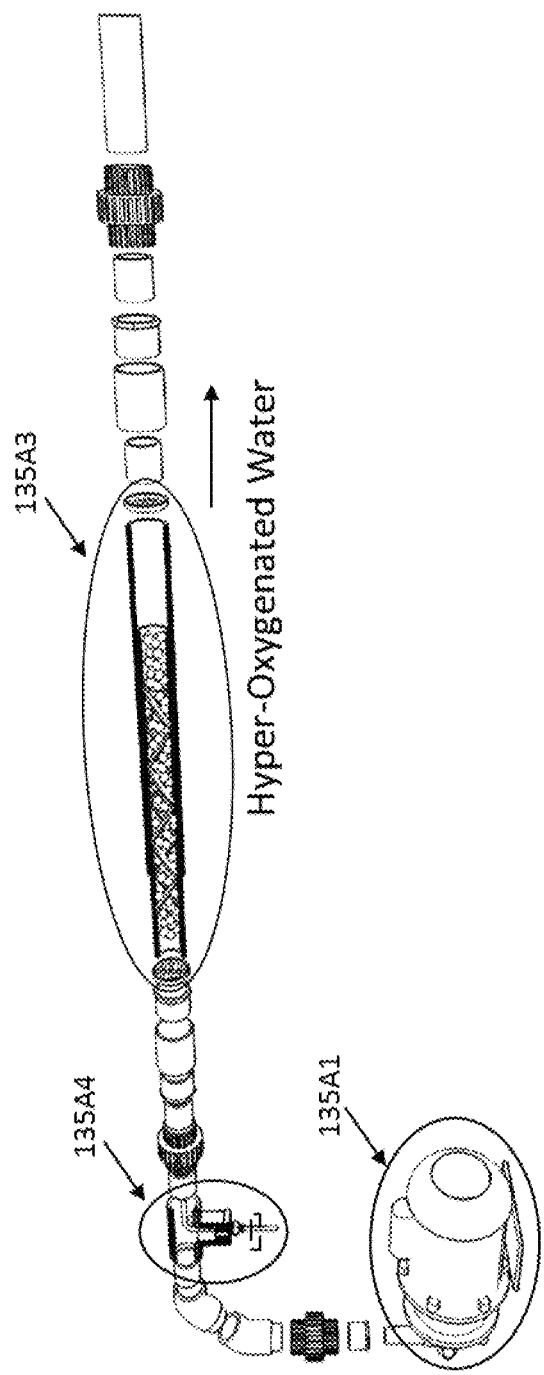
FIG. 8A shows an exemplary illustration of a hyper-oxygenation apparatus including, a high velocity pump, a Tee-joint for mixing oxygen and water in which oxygen is introduced through one perpendicular arm of the Tee-joint, and a vortexing chamber, with an exploded view including a vortexing chamber having cylindrically-shaped housing, in which mineral spheres are arranged in a twisted pattern defined by a series of blades, and the mineral spheres are selected from the group consisting of red ruby, rose quartz, pink quartz, blue quartz, sapphire, emerald, garnet, peridot, aquamarine, spinel, topaz, tanzanite, tourmaline, amethyst, opal, citrine and zircon, or any combinations thereof.

FIG. 8A illustrates in one embodiment details of the oxygenation loop (135) of the hyper-oxygenated water system (100) depicted in FIG. 7. The oxygenation loop (135) forms a closed loop that is configured to raise and sustain predetermined high levels of total oxygen amount in the water composition to the already nanopurified water in the holding tank (120). As can be seen in FIG. 8A, the oxygen loop (135) may comprise a high velocity pump (135A1) configured to push water from the holding tank (120) into the oxygenation loop (135), an oxygen source, which is not shown, configured to supply oxygen for mixing with the water, and a vortexing device (135A3) configured to affect hydrodynamic properties of the water-oxygen mixture so that oxygen nanobubbles are formed in the water.

With continued reference to FIG. 8A, the high velocity pump (135A1) is configured to provide a high velocity flow rate of the water to generate a proper pressure differential of the liquid water passing through a pressure differential injector (135A4) so that oxygen (for example, about 95% $O_2$ molecules) from an oxygen generator (for example, a concentrator or compressor system) can be injected into the water flow. As a result, a high velocity flow of oxygen rich water is fed to the vortexing device (135A3) that is placed immediately after, and at close proximity to, the pressure differential injector (135A4). The high velocity pump (135A1) can pump at a flow rate of more than twenty-five gallons per minute (GPM), preferably at a flow rate of 40-55 GPM.

According to an embodiment of the present disclosure, the vortexing device (135A3) depicted in FIG. 8A may provide a twisted path along a longitudinal direction of the device to provide a vortexing effect to the high velocity flow of oxygen rich water. The twisted path may effectively increase the high velocity flow rate of the oxygen rich water and cause formation of oxygen nanobubbles and oxygen-water clusters within the bulk of water.

According to a further embodiment of the present disclosure, the vortexing device (135A3) may include rose quartz crystal spheres that are seated along the twisted path of the vortexing device, configured to energize the water. As a result, high level oxygen enriched, rose quartz energized water is returned to the holding tank (120). Preferably, the enriched oxygen may be kept at a substantially constant elevated level (e.g., between 10 ppm and 50 ppm) in the water through a closed loop control system that includes a dissolved oxygen concentration meter and membrane sensor. The meter and membrane sensor may work together to start and stop the oxygenation loop (135) any time the dissolved oxygen concentration falls or rises above two preset set points measured, for example, in parts per million (ppm). Alternatively, the enriched oxygen level may be controlled in an open loop fashion through a timer that controls an ON/OFF duty cycle of the oxygenation loop (135).

As shown in FIG. 8B, according to an embodiment of the present disclosure, the oxygen injector device (135A4) may comprise a tubular conduit (135A41), such as, for example, a pipe, made of a metal (e.g., stainless steel, copper, etc.) or a polymer based material (e.g., PVC or other), having one end coupled to the oxygen generator (135A2) for receiving the oxygen, and having the other end immersed in the water having a flow that is provided through the high velocity pump (135A1), wherein the end immersed in the water includes a longitudinal portion of the tubular conduit (135A41) that is substantially parallel to the flow of water. As shown in FIG. 8B, an optional high pressure check valve (135A45) may be provided at an inlet of the pipe (135A41) in order to prevent backflow of the water into the oxygen generator (135A2).

Figure 8C:
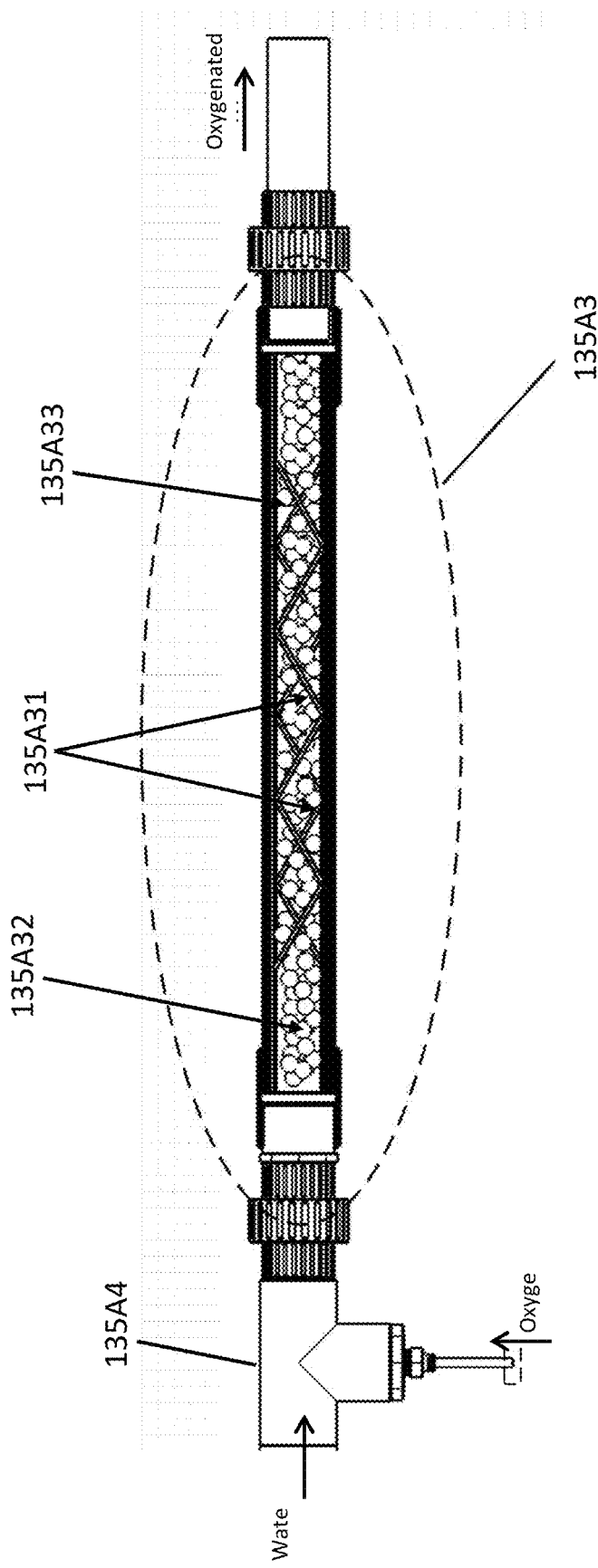
FIG. 8C illustrates details of a vortexing device, according to an embodiment of the present disclosure.

Alternatively, and according to a preferred embodiment of the present disclosure depicted in FIG. 8C, a spiraling effect of the water flow through the vortexing device (135A3) can be provided via two or more series of interconnected baffles (135A31) placed inside of a chamber (135A33) along the longitudinal direction of the vortexing device (135A3), where the two or more series of interconnected baffles (135A31) are configured, in combination, to substantially guide the flow of water inside the chamber (135A33) according to a spiral shaped path. In such configuration, the water is not confined to walls of a spiral shaped physical structure, but rather to the inner wall of the chamber (135A33), and is further diverted by the series of interconnected baffles (135A31) according to a spiral shaped flow path.

According to a further preferred embodiment of the present disclosure, the vortexing device (135A3) may include rose quartz crystal spheres (e.g., 135A32 of FIG. 8C) that are seated along the spiral shaped path of the vortexing device, configured to energize the water. As known to a person skilled in the art, water can be restructured through radiation, or radiant energy, provided by such rose quartz crystal spheres. As a result, high level oxygen enriched, rose quartz energized water is returned to the holding tank (120). Dissolved oxygen in the water of the holding tank (120) may be kept at a substantially constant concentration (e.g., between 10 ppm to 50 ppm) through a closed loop control system that includes a dissolved oxygen concentration meter and membrane sensor. The meter and membrane sensor may work together to start and stop the oxygenation loop (135) any time the dissolved oxygen concentration falls or rises above two preset set points measured, for example, in parts per million (ppm) or mg/L. Alternatively, the dissolved oxygen concentration may be controlled in an open loop fashion through a timer that controls an ON/OFF duty cycle of the oxygenation loop (135).

With further reference to the rose quartz crystal spheres (e.g., 135A32 of FIG. 8C), according to an exemplary embodiment of the present disclosure, such rose quartz crystal spheres can have a diameter between about 15 mm and 20 mm (0.5 inches to 1.0 inches). Mechanical vibration of the crystal spheres due to the high velocity flow of water through the chamber (135A33) of the vortexing device (135A3) can create collisions between the crystal spheres and bubbles of oxygen within the water, therefore resulting in smaller size bubbles to further promote generation of nanobubbles. Furthermore, frequencies associated to said mechanical vibration can cause a greater variation in water pressure through the vortexing device (135A3) which can result in voids, including nano-voids, in the water which can be filled with the smaller size bubbles, including nanobubbles, of oxygen.

Figure 9A:
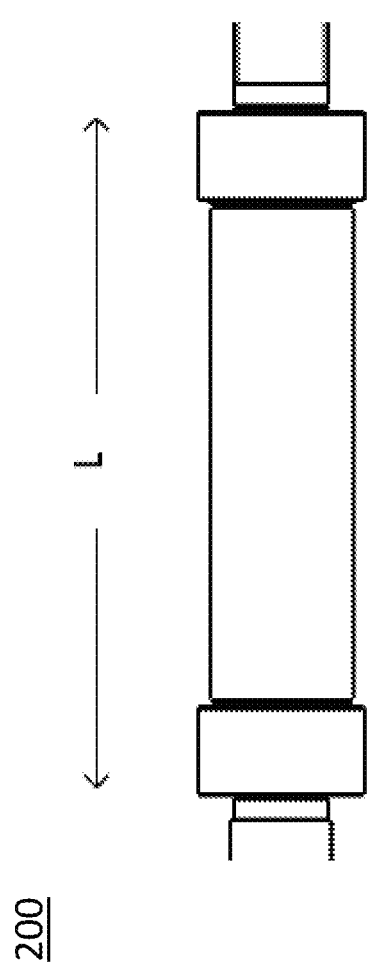
FIG. 9A shows an exemplary illustration of a vortexing device including a vortexing chamber having cylindrically-shaped housing.

FIG. 9A shows an exemplary illustration of a vortexing device (200) including a cylindrically-shaped housing of a longitudinal length L.

Figure 9B:
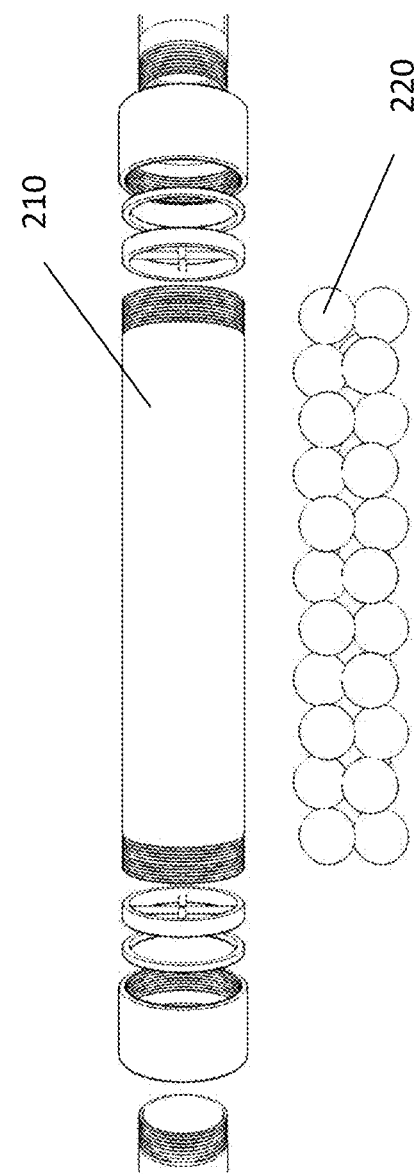
FIG. 9B shows exploded view of the vortexing device in FIG. 9A depicting a vortexing chamber having a plurality of structural impediment objects.

FIG. 9B shows exploded view of the vortexing device in FIG. 9A which a vortexing chamber (210) having a plurality of structural impediment objects (220). The impediment objects can be mineral spheres selected from the group consisting of red ruby, rose quartz, pink quartz, blue quartz, sapphire, emerald, garnet, peridot, aquamarine, spinel, topaz, tanzanite, tourmaline, amethyst, opal, citrine and zircon, or any combinations thereof.

According to some embodiments, a hyper-oxygenated water composition is described. The hyper-oxygenated water composition comprises liquid water, wherein the liquid water is produced by a process of oxygenation to contain a total molecular oxygen in an amount of 10 to 50 ppm and a total dissolved solid of 5 to 200 ppm. In some embodiments, the hyper-oxygenated water composition contains total chlorine in an amount equal or less 1 ppm. In some embodiments, the hyper-oxygenated water composition contains volatile organic compounds (VOCs) in an amount equal or less 1 ppm. In some embodiments, the hyper-oxygenated water composition has the total dissolved solid containing calcium of 1 ppm to 50 ppm, phosphate of 1 ppm to 50 ppm, zinc of 1 ppm to 20 ppm. In some embodiments, the hyper-oxygenated water composition has a temperature range of 4° C. to 40° C. In some embodiments, the hyper-oxygenated water has a total dissolved solid of 5 to 60 ppm. In some embodiments, the hyper-oxygenated water has a temperature range of 30° C. to 40° C., a total molecular oxygen in an amount of 25 to 35 ppm.

In some embodiments, a process of making a hyper-oxygenated water composition is described, the process comprising: providing a source for water having a total dissolved solid of up to 1000 ppm where in the water is subject to steps: (a) pre-filtering the water; (b) purifying the water by absorption; (c) at least partially removing ions from the water by ion exchange; (d) filtering the water by reverse osmosis, wherein the water is caused to flow to a holding tank; (e) ozonolyzing the water in step (d) in an independently circulating fluidic circuit comprising the holding tank and an ozone source; (f) radiating the water in step (d) with ultraviolet light in an independently circulating fluidic circuit comprising the holding tank and an ultraviolet light source; (g) adding a hydrogen peroxide aqueous solution with the ultraviolet light radiated water in step (f); (h) mixing the water in step (d) with oxygen gas in a vortexing chamber in an independently circulating fluidic circuit comprising the holding tank and the vortexing chamber.

The vortexing chamber comprises: a chamber housing having a main hollow channel, a first end and a second end, and a structural mixing medium having one or more three dimensional solid objects, the solid objects having substantially spherical, cubic, rectangular, cylindrical, polyhedron, tetrahedron, or irregular shape, wherein the structural mixing medium is housed within the chamber housing, configured to mix the water and oxygen when the water and oxygen are passed through the vortexing chamber, resulting in a hyper-oxygenation of the water. The hyper-oxygenated water composition in the holding tank contains a total molecular oxygen in an amount of 10 to 50 ppm and a total dissolved solid of 5 to 200 ppm.

Some embodiments, a method for treating or preventing a condition in a subject, the method comprising: administering to the subject in need of the treating or preventing an effective amount of hyper-oxygenated water composition optionally in combination at least one pharmaceutical agent in an effective amount thereof, wherein hyper-oxygenated water composition is produced by a process of oxygenation to contain a total molecular oxygen in an amount of 10 to 50 ppm and a total dissolved solid of 5 to 200 ppm. In some embodiments, administering to the subject is performed transcutaneously.

In some embodiments, a system for hyper-oxygenated water composition is described, the system comprising: a water inlet; a water outlet; a holding tank; a water pre-treatment stage configured to receive water from the water inlet and provide pre-treated water to the holding tank; optionally a water post-treatment stage configured to receive water from the holding tank and provide post-treated water to the water outlet; a water sanitation treatment stage configured to receive water from the holding tank and provide sanitized water to the holding tank; and optionally an oxygenation treatment stage configured to receive water from the holding tank and provide hyper-oxygenated water composition to the holding tank.

In some embodiments, the system includes the water pre-treatment stage comprising: (a) a pre-filter for the water; (b) an absorbent for the water; (c) an ion exchanger; and (d) a reverse osmosis filter. In some embodiments, the system includes the water sanitation treatment stage comprising: (e) an ozone source for producing ozone configured to be mixed with the water in step (d) in an independently circulating fluidic circuit comprising the holding tank and the ozone source; (f) an ultraviolet light source for producing ultraviolet light configured to radiate the water in step (d) in an independently circulating fluidic circuit comprising the holding tank and the ultraviolet light source; and (g) a source of hydrogen peroxide aqueous solution wherein the hydrogen peroxide aqueous solution is metered to be mixed with the ultraviolet light radiated water in step (f).

In some embodiments, the system includes the oxygenation treatment stage comprising: an oxygen gas source, a vortexing chamber in an independently circulating fluidic circuit comprising the holding tank and the vortexing chamber, wherein the vortexing chamber comprises: a chamber housing having a main hollow channel, a first end and a second end, and a structural mixing medium having one or more three dimensional solid objects, the solid objects having substantially spherical, cubic, rectangular, cylindrical, polyhedron, tetrahedron, or irregular shape, wherein the structural mixing medium is housed within the chamber housing, configured to mix the water and oxygen when the water and oxygen are passed through the vortexing chamber, resulting in a hyper-oxygenation of the water.

In some embodiments, the holding tank has a cylindrical body portion in a vertical position, wherein the cylindrical body portion has an open circular portion at the top of the cylindrical body portion and a closed circular portion at the bottom of the cylindrical body portion. In some embodiments, the cylindrical body portion is contiguously made of a material selected from the group consisting of wood, bamboo, plastics, polymers, polyethylene, polypropylene, polybutylene, polychloroprene, polyisoprene, polysulfide, polyvinyl chloride, polystyrene, polyurethane, polycarbonate, nylon, natural rubber, nitrile rubber, iron, steel, stainless steel, food grade stainless steel, type 316 stainless steel, stone, glass, quartz, minerals, and concrete or any combination thereof.

In some embodiments, the holding tank is made of type 316 stainless steel based on SAE steel grades system. Depending on the increasing capacity of the holding tank, the thickness of the type 316 stainless steel ranges from 1/32 inch to 1/2 inch, more preferably from 1/16 inch to 1/4 inch. In some embodiments, when the capacity of the holding tank is less than 400 gallons, the thickness of the type 316 stainless steel is 1/16 inch. When the capacity of the holding tank is 400 gallons to 1000 gallons, the thickness of the type 316 stainless steel is 12 Gauge or about 1/8 inch.

In some embodiments, the holding tank is made of wooden plank. Depending on the increasing capacity of the holding tank, the thickness of the wood plank ranges from 1/2 inch to 3 inches, more preferably from 5/8 inch to 1.5 inches. In some embodiments, when the capacity of the holding tank is less than 400 gallons, the thickness of the wooden plank is 1 inch. When the capacity of the holding tank is 400 gallons to 1000 gallons, the thickness of the type 316 stainless steel is 12 Gauge or about 1/8 inch.

In some embodiments, the cylindrical body portion has a cross section diameter of 0.5 feet to 20 feet and a high of 0.5 feet to 10 feet. Preferably, the cylindrical body portion has a cross section diameter of 3 feet to 10 feet and a high of 1 foot to 5 feet.

In some embodiments, the holding tank further comprises an oxygen sensor and a temperature sensor.

Further characteristics of the present disclosure will become more apparent hereinafter from the following detailed disclosure by way or illustration only with reference to an experimental section.

EXAMPLES

The hyper-oxygenated water and related compositions, methods and systems herein described are further illustrated in the following examples, which are provided by way of illustration and are not intended to be limiting.

In particular, the following examples illustrate exemplary hyper-oxygenated water composition in which molecular oxygen amount in water is in a range from 12 ppm to 50 ppm, 15 ppm to 45 ppm, 20 ppm to 35 ppm or 35 ppm to 50 ppm and related methods and systems. A person skilled in the art will appreciate the applicability and the necessary modifications to adapt the features described in detail in the present section, to additional gases water compositions, methods and systems according to embodiments of the present disclosure.

A skilled person will realize, upon a reading of the present disclosure, that hyper-oxygenated water compositions similar to those exemplified below can be made using the methods for making the hyper-oxygenated water composition herein described. A skilled artisan can select suitable starting material based on the starting materials exemplified below by utilizing databases such as the USPTO's Patent Full-Text and Image Database, GOOGLE, SCIFINDER and REAXYS. A skilled artisan would also be able to use water purification methods known or to be developed in the art in addition to those exemplified below. A skilled person will also realize, that where appropriate, other neutral molecules or salts of different ions can be used in the hyper-oxygenated water composition according to methods known in the art. A skilled person will also realize, that where appropriate, other diseases in addition to those exemplified below can also be ameliorated, prevented or treated by the hyper-oxygenated water compositions.

Example 1: Preparation of Hyper-Oxygenated Water Composition

Described below is the preparation of a hyper-oxygenated water composition. Commercial tap water was treated through several purification procedures.

Ion Exchange and Katoxide

Water was passed through two consecutive purification steps by ion exchange and Katoxide which contains manganese dioxide (in at least 10% gamma form). The Katoxide is a media used in a continuous loop and adapted to remove from water composition suspended solids down to 3 microns in diameter and in addition it can remove color, odor, iron, lead, heavy metals and radio nuclides.

Sediment Filtration

Water was passed consecutively through a 5-micron sediment filter or a 20-micron sediment filter as pre-filter for a reverse osmosis unit. The sediment filters protect the reverse osmosis (RO) membrane from incoming solid particulates.

Reverse Osmosis

Water was passed through a nano-filter of down to 0.0001 microns.

In some exemplary systems, water was purified with a WMH Series Wall Mount High TDS RO System with a UL508A Labeled I-ROC250 controller which was manufactured by Applied Membranes, Inc. at Vista, Calif.

Ozonolysis

A CD10/AD Corona Discharge Ozone Generator manufactured by ClearWater Tech, LLC at San Luis Obispo, Calif. was installed on line for sanitization of water before oxygenation.

Hydrogen Peroxide

Hydrogen peroxide (35% in water, food grade) from Univar at 2600 S Garfield, Los Angeles, Calif. 90040 in a 25 Gallon Black Vertical Water Storage Tank (Ace Roto-Mold of Den Hartog Industries, Inc at Hospers, Iowa) was metered with Bio-Fresh Automatic $H_2O_2$ Activator Feed System at a predetermined flow rate when activated to the stream of water before oxygenation for bathing applications.

Ultraviolet Irradiation

Upstream NC10-50 Ultraviolet Water Purification System manufactured by UV Pure Technologies Inc. at Toronto, Ontario was installed on line to purify water before oxygenation. The Upstream outperforms conventional systems by delivering highly effective UV dosage rates for the inactivation of pathogens, including: viruses, bacteria, *cryptosporidium*, giardia, *legionella, E. coli*, Total coliforms. The Upstream units are laboratory tested to achieve a minimum dose of 40 mJ/cm$^2$.

Oxygen Generation

Oxygen up to 95% purity was provided via a scroll compressor system. The scroll compressor system includes (i) a dissolved oxygen oil less compressor motor which is the driving force that starts the dissolved oxygen process. The oil less compressor motor provides adequate air and pressure to be transformed into oxygen for the dissolved oxygen, DO, process; (ii) a heavy moisture tank which captures and removes any heavy moisture that would disrupt the oxygen production process; (iii) condensation capture and polishing tanks containing three stage tanks which remove any oil/condensation and polish the air entering the oxygen membrane down to 0.003 micron; and (iv) oxygen membrane which is the final membrane that creates oxygen up to 95% purity to be injected into the stream of water in its purified form.

Vortexing-Hyper-Oxygenation

Oxygen up to 99.99% purity, for example of about 95% purity, was mixed water in a vortexer including mineral balls selected from Rose Quartz ball to produced hyper-oxygenated water. The Rose Quartz balls under trade name Gem-inside AAA Grade Madagascar Natural Round Smooth Rose Quartz were purchased from AliExpress under Alibaba Group at https://www.aliexpress.com/. Oxygenation at the exit of the vortexer can be controlled by several factors including flow rate of water, flow rate of oxygen, and temperature. The oxygenation process can be automatically turned off controller device having a preset threshold of entrapped oxygen content which are measured by an oxygen sensor present in a location in the hyper-oxygenated water, preferably a position in the holding tank.

Hyper-Oxygenation in the Bath

The hyper-oxygenated water from the exit of the vortex is conducted to a holding tank to be mixed with a steady volume of hyper-oxygenated water to complete an oxygenation circulation. The level of oxygenation in the bath in automatically controlled through a feedback route.

The level of oxygenation can be measured with Dissolved Oxygen Monitor, Model Q46D-1-2-1-1, purchased from ATI Analytical Technologies, Inc., Collegeville, Pa. 19426.

The holding tank can have a capacity of holding a volume of water from one gallon to two-hundred thousand gallons. In some embodiments, holding tank can be a soaking vessel having a water holding capacity from one to one-thousand gallons. Most preferably, the water holding capacity of the soaking vessel is about seven-hundred gallons.

As used herein, unless otherwise specifically indicated, the dimensions including height, width, length, diameter of a holding tank refers to the interior dimension of the holding tank which is configured to be in direct contact with hyper-oxygenated water.

In some embodiments, a holding tank can be made of material selected from the group consisting of wood, bamboo, plastics, polymers, polyethylene, polypropylene, polybutylene, polychloroprene, polyisoprene, polysulfide, polystyrene, polyurethane, polycarbonate, polyvinyl chloride, nylon, natural rubber, nitrile rubber, iron, steel, stainless steel, food grade stainless steel, stone, glass, quartz, minerals, and concrete or any combination thereof.

In some embodiments, a holding tank can have a quadrilateral cross section in a vertical direction and a horizontal cross section selected from the group consisting of a polygon of 3 to 18 edges, a cyclic polygon of 3 to 18 edges, a circle, an ellipsis. Preferably, the quadrilateral cross section in a vertical direction is identical throughout a height of the holding tank.

In some embodiments, the quadrilateral cross section in a vertical direction is selected from the group consisting of trapezoid, isosceles trapezoid, rectangle, and a square. Preferably, the quadrilateral cross section has a height in a vertical dimension from 10 inches to 100 inches.

In some embodiments, a holding tank can have a cylindrical shape having a height from 10 inches to 100 inches and a cyclic vertical cross section having a diameter from 16 inches to 1600 inches. It is to be understood that a cylindrical shape has a cyclic vertical cross section in a vertical direction which is identical throughout a height of the holding tank.

In some embodiments, a rectangular cuboid holding tank can have a height of at least 10 inches, a width of at least 20 inches and length of at least 30 inches.

As used herein, a rectangle is defined by a length and a width wherein the length has a greater dimension than the width. A golden ratio, as used herein, refers to a length to width ratio of 1:1.617 to 1:1.619, preferably a length to width ratio of 1:1.618. A rectangle conforming to a golden ratio imparts unexpected aesthetic appeals to the rectangle. A distinctive feature of a rectangle having a golden ratio is that when a square section of the width is removed, the remainder is another golden rectangle of corresponding small size, that is, with the same aspect ratio as the first.

In some embodiments, the holding tank can be a rectangular cuboid having a front wall, back wall opposite to the front wall, a left wall, a right wall opposite to the left wall, a bottom face and a top face opposite to the bottom face. Each pair of adjacent walls and/or faces in a rectangular cuboid meets in a right angle. A least one of the front wall, left wall and bottom face can be conformed to the golden ratio in the interior or exterior dimensions of the holding tank.

In some embodiments, a holding tank of a rectangular cuboid can have a left wall and a right wall each of 32" (width)×51.75" (height) (in dimension and a front wall and a back wall of 51.75" (height)×83.75" (length) in dimension such that the four vertical walls comprising front wall, back wall, left wall and right wall are each conformed to the golden ratio. The two horizontal faces comprising a bottom face and a top face are each 32"(width)×83.75" (length) in dimension.

Example 2: Conditioning of Hyper-Oxygenated Water

Biocera Crystal Balls

A hyper-oxygenated water composition was further remineralized by introducing inorganic salts and adjustment of pH values. The hyper-oxygenated water composition was passed through Biocera Crystal Balls from BIOCERA CO., LTD having business address at Bldg C, Korea Bio park, 700 Daewangpangyo-ro, Bundang-gu, Seongnam-si, Gyeonggi-do, South Korea, 13488. The total TDS is increased to 50 ppm after a circulation for 8 hours at a flow rate of 1.5 GPM. The Biocera Crystal Balls have a diameter of 4 mm. The temperature of the hyper-oxygenated water composition was maintained at 37.8° C.

Exemplary Biocera A contains calcium phosphate in the form of hydroxyapatite (i.e. HAP, $Ca_{10}(PO_4)_6(OH)_2$), alumina, silica, zeolite, zinc, and silver ion.

Plant Shell Carbon

A hyper-oxygenated water composition was further passed through a plant shell carbon such as coconut shell carbon or walnut shell carbon. Coconut shell carbon (for example, organic) or walnut shell carbon adsorbs residual volatile or non-volatile organic chemicals, chlorine from water and improve taste of the hyper-oxygenated water. Removal of chlorine additionally avoid the reverse osmosis membrane from potentially being deteriorated by the chlorine.

Example 3: Characterization of Hyper-Oxygenated Water Composition

The presence and stability of nanobubble oxygen is determined by transmission electron microscopy of freeze-fracture replicas of the hyper-oxygenated water composition. [18]. The stable oxygen nanobubbles in the hyper-oxygenated water composition can be measured by Nano Particle Size Analyzer: SALD-7101. [19]. The amount of oxygen in the hyper-oxygenated water composition was measured with ProODO, a handheld optical dissolved oxygen meter from YSI Incorporated in Yellow Springs, Ohio. The hyper-oxygenated water contains in total 10-50 ppm of stabilized oxygen, 5-60 ppm of total dissolved solid (TDS), less than 1 ppm of total chlorine and less than 0.1 ppm of free chlorine.

The presence and amount of ions in water, including hyper-oxygenated composition can be measured by flame atomic absorption using, for example, PinAAcle 900 AA spectrometer which is manufactured by PerkinElmer, Inc. in Waltham, Mass. [9]. The amount of free chlorine and total chlorine can be measured colorimetrically using Thermo Scientific Orion Chlorine XP Water Quality Analyzer. [20]. The hyper-oxygenated water retains stabilized oxygen of at least at 95% purity at 50 ppm initial concentration in 24 hours at 38° C.

Example 4: Skin

Human skin consists of three layers: epidermis, dermis and subcutis. [21]. Stratum corneum is the outermost layer of the epidermis with, on average, about 20 sub-layers of flattened, dead cells depending on where on the body the skin is. These dead cells are shed regularly in a process known as desquamation. The cells in the stratum corneum (i.e., SC) are bound together by epidermal lipids. These lipids are essential for healthy skin: they create its protective barrier and bind in moisture. When lipids are missing, skin can become dry and may feel tight and rough. The composition of the epidermal lipids is dominated by three lipid classes: cholesterol, free fatty acids and ceramides. These lipids adopt a highly ordered, 3-dimensional structure of stacked densely packed lipid layers (lipid lamellae): the lateral and lamellar lipid organization. The way in which these lipids are ordered depends on the composition of the lipids. [22].

Example 5: Skin Permeation by Hyper-Oxygenated Water

The oxygen permeability of skin tissue is strongly dependent upon water content. [23]. The continuous lipid matrix in stratum corneum provides the main barrier against water loss. [24]. The same barrier against water loss also plays the rule of controlled modulation of water and/or oxygen infiltration into the body through skin. Transcutaneous oximetry and near infrared spectroscopy was used to measure changes in skin molecular oxygen concentration. It is unexpectedly found that hyper-oxygenated water facilitates delivery of the entrained oxygen in the hyper-oxygenated water through the stratum corneum.

With a super-oxygenated water having total molecular oxygen at 30 ppm and 50 ppm and a temperature of 38° C., the rate of oxygen absorption through human skin are approximately 3 $mLm^{-2} min^{-1}$ and 5 $mLm^{-2} min^{-1}$, respectively. Other things being equal, the rate of oxygen absorption through human skin increases with the concentration of oxygen in a linear relationship.

Example 6: Oral Administration of Hyper-Oxygenated Water Composition

Hyper-oxygenated water composition was orally administered to a subject in need thereof in an therapeutically or preventively effective amount. The subject was inflicted or predisposed to be inflicted with a condition selected from the group consisting of edema, emphysema, congestive heart failure, muscular and sclerosis. Additional suitable medical applications will be identifiable by a skilled person with particular reference to applications in which biological oxygenation process is desired.

Hyper-oxygenated water composition may be administered once a day (OD), twice a day (BID), three times a day (TID), four times a day (QDS) or more often as necessary at dosage from 15 mL to 1500 mL a day, depending on the age, weight, disease condition of the subject as will be understood by a skilled person in the art. Hyper-oxygenated water composition may be administered once a day, the composition can be administered at any time of the day, when the administration is two times a day, morning and evening administration can be chosen, when the administration is three times a day, morning, noon and evening administration can be chosen. Hyper-oxygenated water composition may be administered in equal dosages each time. For example, if the daily dosage is 450 mL and on a twice a day schedule, each time 225 mL would be administered orally.

Alternatively, hyper-oxygenated water composition was administered in different dosages each time. For example, if the daily dosage is 450 mL and was on a twice a day schedule, in the first time 300 mL of hyper-oxygenated water composition was administered orally in the morning and in the second time 150 mL of hyper-oxygenated water composition was administered orally in the evening. Timing and dosages of oral administration of hyper-oxygenated water composition to treat and/or prevent the condition can vary depending on the subject, the effect to be achieved (treatment and/or prevention of the condition) and the severity of the condition as will be understood by a skilled person. The subject may be orally administered hyper-oxygenated water composition for a duration of at least one week, one month, one year or 3 year or lifetime.

Example 7: Transcutaneous Administration Hyper-Oxygenated Water Composition

Hyper-oxygenated water composition may be transcutaneous administered to a subject in need thereof in an therapeutically or preventively effective amount. The subject may be inflicted or predisposed to be inflicted with a condition selected from the group consisting of edema, emphysema, congestive heart failure, muscular and sclerosis. Additional suitable medical applications will be identifiable by a person of ordinary skill in the art with particular reference to applications in which biological oxygenation process is beneficial.

A hyper-oxygenated water composition of the present invention including 10 ppm to 50 ppm of oxygen may be administered once a day (OD), twice a day (BID), three times a day (TID), four times a day (QDS) or more often as necessary at dosage from 15 mL to 1500 mL a day, depending on the age, weight, disease condition of the subject as will be understood by a skilled person in the art. A hyper-oxygenated water composition may be administered once a day, wherein the composition can be administered at any time of the day. When the administration is two times a day, morning and evening administration can be chosen, and when the administration is three times a day, morning, noon and evening administration can be chosen.

A hyper-oxygenated water composition of the present invention may be administered in equal dosages each time. For example, if the daily dosage is 450 mL and was on a twice a day schedule, each time 225 mL would be administered orally. Alternatively, hyper-oxygenated water composition may be administered in different dosages each time. For example, if the daily dosage is 450 mL and was on a twice a day schedule, in the first time 300 mL of hyper-oxygenated water composition was administered orally in the morning and in the second time 150 mL of hyper-oxygenated water composition may be administered orally in the evening. The subject may be transcutaneously administered hyper-oxygenated water composition for a duration of at least one week, one month, one year or 3 year or lifetime. Timing and dosages of administration of hyper-oxygenated water composition to treat and/or prevent the condition can vary depending on the subject, the effect to be achieved (treatment and/or prevention of the condition) and the severity of the condition as will be understood by a person of ordinary skill in the art.

Example 8: Treatment of Human Diseases

Hyper-oxygenated water composition was used accelerate the healing and regeneration damaged tissue by oral administration or transcutaneous administration by immersion in a soaking vessel. Soaking supplies sufficient quantities of oxygen in the form of hyper-oxygenated water to wound area in the external portion of body. Such wounds include cuts, lacerations, sores and burns on the face, arms, legs, torso and roof of the mouth. Hyper-oxygenated water compositions of the present invention may also used to treat or mitigate diseases selected from the group consisting of edema, emphysema, congestive heart failure, muscular and sclerosis by oral administration, optionally in combination with soaking.

Example 9: Maintenance of Human Well-being

A hyper-oxygenated water composition of the present invention may be used in topical applications for cleaning and revitalizing skin. In facial cleansing, hyper-oxygenated water composition assisted in exfoliating dead skin particles from the skin surface. Hyper-oxygenated water composition lightened the contacted skin that has been affected by hyperpigmentation. Hyper-oxygenated water composition remove toxins, particulates and other occlusions in skin pores. Without being bound by theory, oxygen oxidized oil molecules in the skin pores, thus allowing the pores to become backfilled with water. Once the skin is removed and dried, the pores would be accessible to infilltration by beneficial lotions and other skin care products. Skin topography (roughness) will be improved following exposure of the skin to hyper-oxygenated water composition. Peaks that existed in the epidermal layer of a skin will become smooth, without being bound by theory, as a result of selectively higher oxidation rates associated with higher surface area ridges of the skin.

The examples set forth above are provided to give those of ordinary skill in the art a complete disclosure and description of how to make and use the embodiments hyper-oxygenated water and related compositions, methods, and systems of the disclosure, and are not intended to limit the scope of what the Applicant regards as its disclosure. Modifications of the above-described modes for carrying out the disclosure can be used by persons of skill in the art, and are intended to be within the scope of the following claims.

The entire disclosure of each document cited (including patents, patent applications, journal articles including related supplemental and/or supporting information sections, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The term "hyper-oxygenated" as used herein refers to a liquid water that contains molecular oxygen in a meta-stabilized state that is 0.5 ppm or higher than the thermodynamically determined oxygen saturation concentration of the liquid water. [25].

As used herein, meta-stabilized state refers to a stable state of a dynamical system other than the system's state of least energy. [26].

A hyper-oxygenated water as described herein can have a total molecular oxygen concentration ranging from 12 ppm to 50 ppm, 15 ppm to 45 ppm, 20 ppm to 35 ppm or 35 ppm to 50 ppm at a temperature between 20 to 35° C.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure.

Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure.

The term "stable", as used herein, refers to a property of composition that is not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Wikipedia, *Air pollution*, accessed on May 26, 2017 at https://en.wikipedia.org/wiki/Air_pollution. 2017: p. 1-26.
2. Ladizinsky, D. and D. Roe, *New Insights Into Oxygen Therapy for Wound Healing.* Wounds, 2010. 22(12): p. 294-300.
3. *Hyperbaric oxygen therapy*, accessed on May 24, 2017 at http://www.mayoclinic.org/tests-procedures/hyperbaric-oxygen-therapy/basics/definition/prc-20019167. 2017: p. 1-3.
4. Crandall., J. J., et al., U.S. Pat. No. 6,284,293 B1.
5. Ebina, K., et al., *Oxygen and air nanobubble water solution promote the growth of plants, fishes, and mice.* PLoS One, 2013. 8(6): p. e65339.
6. Chiba, K., US 2007/0286795A1.
7. Eckert, C. E., U.S. Pub. No.: 2013/0041312 A1.
8. Holloway, M. A., U.S. Pat. No. 6,521,248 B1.
9. Spivey, N., *Application Note, Atomic Absorption, Analysis of Major Elements in Drinking Water Using FAST Flame Sample Automation for Increased Sample Throughput.* 2015: p. 1-5.
10. Ignatov, I. and O. Mosin, *Structural mathematical models describing water clusters.* Journal of, 2013.
11. Stillinger, F. H., *Theory and molecular models for water.* Adv. Chem. Phys, 1975. 31(1).
12. Kasai, Y., et al., *The H2OO2 water vapour complex in the Earth's atmosphere.* Atmospheric Chemistry and Physics, 2011. 11(16): p. 8607-8612.
13. United States Environmental Protection Agency, *METHOD 8265, Volatile Organic Compounds In Water, Soil, Soil Gas, And Air By Direct Sampling Ion Trap Mass Spectrometry (DSITMS).* 2002: p. 1-64.
14. Yin, H., G. Hummer and J. C. Rasaiah, *Metastable water clusters in the nonpolar cavities of the thermostable protein tetrabrachion.* Journal of the American Chemical Society, 2007. 129(23): p. 7369-7377.

15. Potts, R.O. and M. L. Francoeur, *Lipid biophysics of water loss through the skin*. Proceedings of the National Academy of Sciences, 1990. 87(10): p. 3871-3873.
16. Reading, S., M. Yeomans, and C. Levesque, *Skin oxygen tension is improved by immersion in oxygen-enriched water*. International journal of cosmetic science, 2013. 35(6): p. 600-607.
17. Reading, S. A. and M. Yeomans, *Oxygen absorption by skin exposed to oxygen supersaturated water*. Canadian journal of physiology and pharmacology, 2012. 90(5): p. 515-524.
18. Uchida, T., et al., *Effect of NaCl on the Lifetime of Micro-and Nanobubbles*. Nanomaterials, 2016. 6(2): p. 31.
19. Shimadzu, *Application New, Nano Particle Size Analyzer: SALD-7101*, No. 4, Down Loaded from: http://www.ssi.shimadzu.com/products/literature/testing/microbubbles%20nanobubbles%20red.pdf on Jul. 24, 2017. p. 1-3.
20. *Thermo Scientific Orion Chlorine XP Water Quality Analyzer* UM-269688-001 Revision C. 2016: p. 1-57.
21. Eucerin, *Understanding skin*, accessed on Jun. 5, 2017 at http://www.eucerin.sg/about-skin/basic-skin-knowledge/skin-structure-and-function. p. 1-15.
22. van Smeden, J., et al., *Stratum corneum lipids: their role for the skin barrier function in healthy subjects and atopic dermatitis patients*, in *Skin Barrier Function*. 2016, Karger Publishers. p. 8-26.
23. Stücker, M., et al., *The cutaneous uptake of atmospheric oxygen contributes significantly to the oxygen supply of human dermis and epidermis*. The Journal of physiology, 2002. 538(3): p. 985-994.
24. Das, C., et al., *The physics of stratum corneum lipid membranes*. Phil. Trans. R. Soc. A, 2016. 374 (2072): p. 1-13.
25. Battino, R., et al., *The solubility of oxygen and ozone in liquids*. Journal of physical and chemical reference data, 1983. 12(2): p. 163-178.
26. Wikipedia, *Metastability*, accessed on Jun. 5, 2017 at https://en.wikipedia.org/wiki/Metastability. 2017.

What is claimed is:

1. A system for hyper-oxygenated water composition, the system comprising:
    a water inlet;
    a water outlet;
    a holding tank;
    a water pre-treatment stage configured to receive water from the water inlet and provide pre-treated water to the holding tank;
    optionally a water post-treatment stage configured to receive water from the holding tank and provide post-treated water to the water outlet;
    a water sanitation treatment stage configured to receive water from the holding tank and provide sanitized water to the holding tank; and
    an oxygenation treatment stage configured to receive water from the holding tank and provide hyper-oxygenated water composition to the holding tank,
    wherein the oxygenation treatment stage includes an oxygen gas source, a vortexing chamber in an independently circulating fluidic circuit comprising the holding tank and the vortexing chamber, and wherein the vortexing chamber includes a chamber housing having a main hollow channel, a first end and a second end, and a structural mixing medium having one or more three dimensional solid objects, the solid objects having substantially spherical, cubic, rectangular, cylindrical, polyhedron, tetrahedron, or irregular shape, wherein the structural mixing medium is housed within the chamber housing, configured to mix the water and oxygen when the water and oxygen are passed through the vortexing chamber, resulting in a hyper-oxygenation of the water.

2. The system of claim 1, wherein the water pre-treatment stage includes a pre-filter for the water; an absorbent for the water; an ion exchanger; and a reverse osmosis filter.

3. The system of claim 2, wherein the water sanitation treatment stage includes an ozone source for producing ozone configured to be mixed with the water in an independently circulating fluidic circuit comprising the holding tank and the ozone source; an ultraviolet light source for producing ultraviolet light configured to radiate the water in an independently circulating fluidic circuit comprising the holding tank and the ultraviolet light source; and a source of hydrogen peroxide aqueous solution wherein the hydrogen peroxide aqueous solution is metered to be mixed with the ultraviolet light radiated water.

4. The system of claim 1, wherein the holding tank has a flat bottom and is configured to hold a body of water having a depth of at least 0.10 meters, a surface width of at least 0.20 meters and a surface length of 0.3 meters at the top of the body of water.

5. The system of claim 4, wherein the tank has a bottom width of at least 0.10 meters and a bottom length of 0.15 meters at the bottom of the body of water.

6. The system of claim 1, wherein the holding tank has a cylindrical body portion in a vertical position, wherein the cylindrical body portion has an open circular portion at the top of the cylindrical body portion and a close circular portion at the bottom of the cylindrical body portion.

7. The system of claim 6, wherein the cylindrical body portion is contiguously made of a material selected from the group consisting of wood, bamboo, plastics, polymers, polyethylene, polypropylene, polybutylene, polychloroprene, polyisoprene, polysulfide, polyvinyl chloride, polystyrene, polyurethane, nylon, natural rubber, nitrile rubber, iron, steel, stainless steel, food grade stainless steel, stone, glass, quartz, minerals, concrete, and any combination thereof.

8. The system of claim 6, wherein the cylindrical body portion has a cross section diameter of 0.2 meters to 10 meters and a height of 0.2 meters to 5 meters.

9. The system of claim 1, wherein the holding tank further comprises an oxygen sensor and a temperature sensor.

10. A system for hyper-oxygenated water composition, the system comprising:
    a water inlet;
    a water outlet;
    a holding tank;
    a water pre-treatment stage configured to receive water from the water inlet and provide pre-treated water to the holding tank;
    optionally a water post-treatment stage configured to receive water from the holding tank and provide post-treated water to the water outlet;
    a water sanitation treatment stage configured to receive water from the holding tank and provide sanitized water to the holding tank;
    an oxygenation treatment stage configured to receive water from the holding tank and provide hyper-oxygenated water composition to the holding tank, wherein the hyper-oxygenated water composition comprises at least 20 ppm of molecular oxygen at a temperature ranging from 4 to 50° C., wherein the oxygenation treatment stage includes an oxygen gas source, a vortexing chamber in an independently circulating fluidic circuit comprising the holding tank and the vortexing chamber, and wherein the vortexing chamber includes a chamber housing having a main hollow channel, a first end and a second end, and a structural mixing medium having one or more three dimensional solid objects, the solid objects having substantially spherical, cubic, rectangular, cylindrical, polyhedron, tetrahedron, or irregular shape, wherein the structural mixing medium is housed within the chamber housing, configured to mix the water and oxygen when the water and oxygen are passed through the vortexing chamber, resulting in a hyper-oxygenation of the water.

11. The system of claim 10, wherein the hyper-oxygenated water composition comprises 20 to 35 ppm of molecular oxygen.

12. The system of claim 10, wherein the hyper-oxygenated water composition comprises 35 to 50 ppm of molecular oxygen.

* * * * *